United States Patent
Nielsen et al.

(10) Patent No.: US 8,961,854 B2
(45) Date of Patent: Feb. 24, 2015

(54) URISHEATH WITH MOULDED UNROLLING STRIP

(75) Inventors: Henrik Lindenskov Nielsen, Smoerum (DK); Johan Christiansson, Horby (SE); Peter Persson, Horby (SE)

(73) Assignee: Nolato Meditech AG, Hoerby (SE)

( * ) Notice: Subject to any disclaimer, the term of this patent is extended or adjusted under 35 U.S.C. 154(b) by 921 days.

(21) Appl. No.: 13/160,090

(22) Filed: Jun. 14, 2011

(65) Prior Publication Data

US 2011/0257615 A1    Oct. 20, 2011

Related U.S. Application Data

(62) Division of application No. 12/281,219, filed as application No. PCT/EP2007/051916 on Feb. 28, 2007, now Pat. No. 8,795,258.

(60) Provisional application No. 60/794,119, filed on Apr. 24, 2006.

(30) Foreign Application Priority Data

Mar. 1, 2006  (DK) .................................. 2006 00297

(51) Int. Cl.
*B29C 45/03* (2006.01)
*A61F 5/453* (2006.01)
*A61F 6/04* (2006.01)

(52) U.S. Cl.
CPC ........... *A61F 5/453* (2013.01); *A61F 2006/049* (2013.01)
USPC .......................... 264/295; 264/328.1; 425/577

(58) Field of Classification Search
CPC .......................... A61F 2006/049; A61F 5/453
USPC ................ 264/328.1, 279, 295; 425/542, 577
See application file for complete search history.

(56) References Cited

U.S. PATENT DOCUMENTS

| 3,608,552 A | 9/1971 | Broerman |
| 3,835,857 A | 9/1974 | Rogers, III et al. |
| 3,901,965 A | 8/1975 | Honeyman |

(Continued)

FOREIGN PATENT DOCUMENTS

| EP | 162037 A2 | 11/1985 |
| EP | 710535 A1 | 5/1996 |

(Continued)

OTHER PUBLICATIONS

English translation of Japanese Office Action dated Jan. 5, 2012 for JP Application No. 2008-556777.

(Continued)

*Primary Examiner* — Jill Heitbrink
(74) *Attorney, Agent, or Firm* — Martin & Ferraro, LLP (57) ABSTRACT

The urisheath provided here includes an element of thin material (a strip) that allows at least two lengths of it to run in a parallel fashion down either side of the sheath. The is obtained by injection molding the strip in liquid silicone in the silicone injection molding process for the urisheath, either by one, two or more component injection molding. The injection molding takes place in an injection molding form for a urisheath with a cavity for the body portion and a cavity for the strip portion wherein the cavity for the body portion is connected to the cavity for the strip portion creating an attachment zone between the strip and the sheath.

14 Claims, 5 Drawing Sheets

(56) References Cited

U.S. PATENT DOCUMENTS

| | | | |
|---|---|---|---|
| 4,149,695 | A | 4/1979 | Quick et al. |
| 4,581,026 | A | 4/1986 | Schneider |
| 4,594,761 | A | 6/1986 | Murphy et al. |
| 4,732,724 | A | 3/1988 | Stemer |
| 4,734,241 | A | 3/1988 | Gerow |
| 4,872,463 | A | 10/1989 | Nishizono |
| 4,934,382 | A | 6/1990 | Barone, Jr. |
| 5,554,141 | A | 9/1996 | Wendler |
| 5,685,870 | A | 11/1997 | Tanghoj |
| 5,713,880 | A | 2/1998 | Anderson |
| 6,250,303 | B1 | 6/2001 | Delaney |
| 6,376,432 | B1 | 4/2002 | Leslie et al. |
| 6,726,363 | B1 | 4/2004 | Marbler |
| 6,805,690 | B2 | 10/2004 | Ogden et al. |
| 2002/0026163 | A1* | 2/2002 | Grundke .................. 604/347 |
| 2005/0101923 | A1 | 5/2005 | Elson et al. |
| 2008/0215021 | A1 | 9/2008 | Cisko Jr. et al. |
| 2009/0018530 | A1 | 1/2009 | Nielsen et al. |
| 2009/0118688 | A1 | 5/2009 | Nielsen et al. |
| 2011/0118685 | A1 | 5/2011 | Nielsen et al. |

FOREIGN PATENT DOCUMENTS

| | | |
|---|---|---|
| EP | 979718 A1 | 2/2000 |
| EP | 1 063 007 A1 | 12/2000 |
| FR | 2 374 754 | 12/1996 |
| FR | 2771923 | 6/1999 |
| GB | 2 357 725 | 7/2001 |
| JP | 57-209051 A | 12/1982 |
| JP | 58-001445 A | 1/1983 |
| JP | 58001529 A | 1/1983 |
| JP | 60-229716 A | 11/1985 |
| JP | 61/277419 A | 12/1986 |
| JP | 62-070012 A1 | 3/1987 |
| JP | 01 110116 A | 4/1989 |
| JP | 3-33617 U | 4/1991 |
| JP | 03-033617 U | 4/1991 |
| JP | 4-19117 | 1/1992 |
| JP | 5-506381 A | 9/1993 |
| JP | 7-002019 U | 1/1995 |
| JP | 8-336842 A | 12/1996 |
| JP | 10183162 A | 7/1998 |
| JP | 10-291235 A | 11/1998 |
| JP | 2002-102110 A | 4/2002 |
| JP | 2003-211500 A | 7/2003 |
| JP | 2008-511360 A | 4/2008 |
| JP | 2008-543423 A | 12/2008 |
| WO | WO 91/17728 A1 | 11/1991 |
| WO | PCT/US91/08432 | 5/1992 |
| WO | WO-92/08426 A1 | 5/1992 |
| WO | WO 93/03697 A1 | 3/1993 |
| WO | WO-97/40790 | 11/1997 |
| WO | WO-98/22275 | 5/1998 |
| WO | WO 02/053070 A1 | 7/2002 |
| WO | WO 2004/004796 A1 | 1/2004 |
| WO | WO 2006/024637 | 3/2006 |
| WO | WO 2007/040441 | 4/2007 |
| WO | WO 2007/099129 | 9/2007 |

OTHER PUBLICATIONS

G. Steinbichler, "Spritzgeissen VonFluessigsiliconkautschuk", Kunststoffe, Carl Hanser Verlag, Muenchen, Germany, XP001176509, vol. 77, No. 10, pp. 931-933 (Oct. 1, 1997).

International Search Report, mailed Oct. 10, 2007.

* cited by examiner

URISHEATH WITH MOULDED UNROLLING STRIP

This is a division of application Ser. No. 12/281,219, filed Sep. 22, 2008, the entire contents of which are incorporated herein by reference.

BACKGROUND

External urinary catheters, also known as urisheaths, are conventionally used in urinary catheter devices for aiding male urinary incontinence and for use in hospitals in connection with treatment and surgery of urethral disorders. Such an external urinary catheter normally comprises a sheath or body portion enclosing the shaft of the penis, and a tip portion that is provided with a comparatively short discharge tube, which via a tube is connected to a urine collection bag that is e.g. fastened to the bed or the leg of the user. Unrolling a sheath correctly on a penis can be very challenging. This procedure is often performed by users with poor dexterity or by hospital staff wearing protective gloves for hygienic reasons. However, it is essential that the sheath be fitted correctly to ensure a leak proof seal between the skin and the sheath. Problems occur if the sheath does not unroll evenly or if the protective gloves stick to the sheath adhesive.

One present solution to this problem is a single strip assisting application of the sheath. However, this strip pulls only on one side of the sheath, which causes uneven roll and is difficult to hold with poor dexterity.

By using an injection-molding machine, the wall thickness of the product may be controlled very precisely by the design of the cavity of the injection-molding machine. Thus, a thin-walled product of high quality can be produced by this method.

SUMMARY

The solution to the problem of unrolling a urisheath provided here thus includes an element of thin material that allows at least two lengths of it to run in a parallel fashion down either side of the sheath. The two lengths of the element, the strips, are rolled with the sheath. The top end of the element towards the sheath tip is preferably formed as a loop big enough to grab and pull with a male thumb (the handle). When pulling the loop in a downward motion (that is from the sheath tip towards the opposite end of the sheath), the sheath is unrolled evenly. With the double action strip, the sheath is more easily unrolled onto the penis in an even fashion and without having to touch the adhesive. However, attaching this strip to the product is difficult and is done manually by very skilled operators. This manual operation is very costly. Automation of this process is considered also to be very costly too.

The solution to this problem is to injection mould the strip in liquid silicone in the silicone injection moulding process for the urisheath, either by one, two or more component injection moulding.

DETAILED DISCLOSURE

One aspect of the invention relates to a urisheath semi-manufacture product comprising a body portion and a strip portion wherein the strip portion is attached to the body portion in an attachment zone. The body portion extends from the urine outlet (a tip part) and an open end. The tip part is where the urine leaves the urisheath. This is preferably a comparatively short discharge tube. To this discharge tube, a drainage tube is often attached. The other end of the drainage tube is typically connected to a urine collection bag.

The attachment zone may be provided in a number of different ways; such as for example being formed as weakened zones, having lower tear strength than the strip portion and the urisheath respectively. Such weakened zones are typically formed of the same material as the strip portion and the urisheath, and having a smaller thickness than the strip portion and the urisheath.

Thus, when pulling the strip portion and the urisheath away from each other they will advantageously separate at the attachment zone.

Further alternative attachment zones may be provided by for example different types of materials having a tear strength which is smaller than that of the material of the strip portion and the material of the urisheath. Two-component injection moulding will produce such products.

The urisheath preferably further comprises adhesive on the inside to attach and seal to the penis. The urisheath preferably further comprises a flexible zone between the tip part and the body portion.

Figure 2:
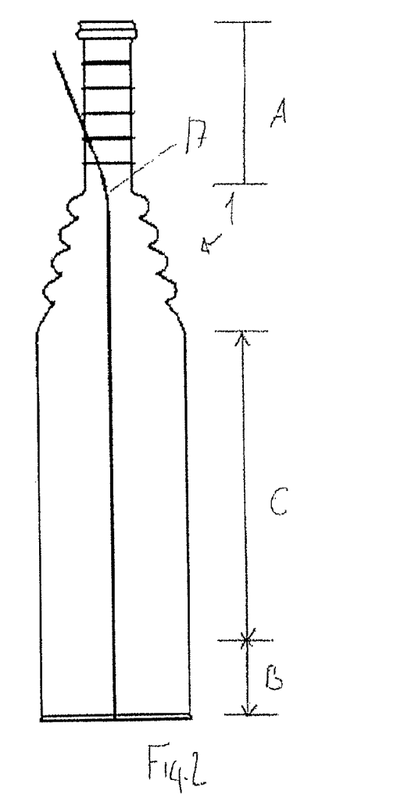

The tip part can be the top 3 cm of the entire urisheath (A on FIG. 2). Preferably that is ⅓ of the entire length of the urisheath (not including optional flexible zones). The root part of the urisheath is the part of the urisheath extending from the open end to ⅓ of the entire body portion (B on FIG. 2). The section between the tip portion and the root portion (excluding optional flexible zones) is referred to as the centred part (C on FIG. 2).

Such urisheath is injection moulded with an injection moulding form for a urisheath comprising a body portion and a strip portion, the form comprising a cavity for the body portion and a cavity for the strip portion wherein the cavity for the body portion is connected to the cavity for the strip portion. This form preferably comprises three parts: a core part, an upper shield part and a lower shield part.

In one embodiment, the strip portion comprises one strip. One strip is sufficient to unroll the urisheath on the penis. In another embodiment, the strip portion comprises two strips. Having two strips, preferably at opposite sides of a tubular urisheath, an even draw when applying the urisheath is obtained.

Such urisheath is injected moulded with an injection moulding form wherein the cavity for the strip portion comprises one strip. Alternatively, the cavity for the strip portion comprises two strips. The form with cavities for two strips preferably comprises these cavities diagonally across from each other, that are in the dividing line between the two shield parts.

It is troublesome to connect and align a strip on the urisheath before rolling the urisheath in a ready-to-use configuration. In one aspect of the present invention, the strip portion is attached to the body portion at the root part and at the tip part. That is, if there are two strips, each strip is attached to the body portion at the root part and at the tip part of the urisheath. Whether a continuous attachment or a point-like attachment, the strip will be oriented along the longitudinal direction of the urisheath. Hence easy connection and alignment of the strip(s) on the urisheath before rolling the urisheath in a ready-to-use configuration is obtained.

Such a urisheath is injected moulded with an injection moulding form wherein the connection between the cavity for the strip portion and the cavity for the body portion is at the root part.

The user will experience the attachment zones as resistance during the application of the urisheath. Thus, the balance between easy rolling of the urisheath during production on the one side, and the degree of resistance offered to the user on the other. In one embodiment, the strip portion is attached to the body portion at the root part, the centred part and at the tip part. In another embodiment, the strip portion is attached to the body portion along the entire centred portion. In yet another embodiment, the strip portion is attached to the body portion along the entire root- and centred portions and with a point like attachment to the tip portion.

Such a urisheath is injected moulded with an injection moulding form wherein the connections between the cavity for the body portion and the cavity for the strip portion are wider (in the urisheath longitudinal direction). That is, one form wherein there are connections between the cavity for the body portion and the cavity for the strip portion at the root part, the centered part and at the tip part. In another form, there is a connection between the cavity for the body portion and the cavity for the strip portion along the entire centred portion. In yet another moulding form, there is a connection between the cavity for the body portion and the cavity for the strip portion along the entire root- and centered portions and with a point like connection at the tip portion.

In a preferred embodiment, the attachment zone(s) between the body portion and the strip portion has lower tear strength than the body portion and the strip portion. Hence the result obtained is that when pulling the strip portion, the strip portion is detached from the body portion without destroying either the body portion or the strip portion.

Such a urisheath is injected moulded with an injection moulding form wherein the connection between the cavity for the body portion and the cavity for the strip portion is sufficiently thin, so that the mass of the material to be broken is small, that is the material in the attachment zone is thin.

In an alternative embodiment, the attachment zones are broken, e.g. cut, just before rolling the urisheath. One example is a continuous detachment and rolling process.

In the design of certain moulding forms, it is troublesome to join the two strips along side the urisheath. Thus, in one embodiment of the invention, the strip portion comprises two strips with attachment means for joining the two strips at the tip part of the strips.

Such a urisheath is injected moulded with an injection moulding form wherein each of the cavities for the strips comprises indentations providing attachment means for joining the two strips. An example of such attachment means is a hole in one strip and a hook on the other strip.

An alternative embodiment thereof, a separate handle is attached to the two strips after injection moulding.

In one embodiment of the invention, at least two strips are joined outside the rolled tubular section. This provides for one major advantage of the present invention: for example urisheath users with poor dexterity will now be able to apply the urisheath themselves, without outside help by only using one hand. This is a major break-through to the self-esteem of these users. In a further embodiment joint strips form a handle for unrolling the rolled tubular section. In an even further embodiment the joint strips form a finger-pull-hole. Such finger-pull-hole enables the user of for example an urisheath to insert a finger, and pull. Whereas an ear handle requires two fingers, and force between those, (tweezers grip), the ring only requires a pull force. Thus, it is preferred that the strip portion comprises two strips and further comprises a handle connecting the two strips. Preferably, the handle is thicker than the strips.

In one embodiment, the handle is positioned below the urisheath (see FIGS. 6 and 7), i.e. the strips extend from the root part in a direction away from the tip part. This position of the handle is preferably secured through the attachment zone in the root part. A width of the strips are attached to the root part, preferably the width is 1 mm that is more than 0.1 mm. This will make rolling of the device automated as one robot arm grab the urisheath and a hook grabs the handle providing resistance during rolling of the urisheath, whereby tangling of the strips is avoided.

For the injection moulding of a urisheath further comprising a handle portion, an injection moulding form further comprising a cavity for the handle portion is required. One example of such form is an injection moulding form wherein the cavity for the strip portion is located in longitudinal continuation of the cavity for the body portion and the cavity for the handle portion located to connect the strips.

In another embodiment, the handle is positioned above the tip portion, i.e. the strips extend from the root part in a direction towards the tip part. Such urisheath is injected moulded with an injection moulding form wherein the cavities for the strips terminate in a cavity for the handle above the tip portion. Having this handle in the centerline of the body portion enables that opening of the moulding forms will then reveal the strip portion.

In yet another embodiment, the handle is positioned beside the tip portion. Such urisheath is injected moulded with an injection moulding form wherein the cavity for the handle portion is sufficiently thick such that the cured material in this cavity can be pulled out (blown out). In one embodiment the cavity for the handle portion is thicker than the strip portion in general. An alternative injection moulding form comprises four parts: the forth part being between the two shield parts such that the cavity for the handle portion can be opened and the product removed from the cavity.

In one embodiment the handle it attached to the tip portion. This embodiment requires a subsequent dividing process. This can be carried out before rolling, after rolling, or even by the user.

It is preferred that the body portion is a silicone body portion.

To obtain the desired performance of the strip to un-roll the urisheath onto the penis, a strip material with sufficient release from the sheath adhesive has to be used. It is preferred that the strip is moulded in silicone.

The strip portion can be moulded in various hardness and types of silicone materials. In one embodiment the material is the same material, as the material used for the body portion. Particularly preferred for this is silicone C6-540 silicone from Dow Corning.

However, two-component injection moulding is feasible and enables attachment of the materials in liquid/non-vulcanised form. If 2-component moulding is used, it is preferred, that the strip is made in a harder silicone than the urisheath part. The preferred materials for the strip portion are platinum cured LSR silicones that give sufficiently release to the urisheath adhesive also after prolonged ageing. Particularly preferred is silicone C6-570 silicone from Dow Corning.

One aspect of the invention relates to a method for producing a urisheath comprising a body portion and a strip portion, comprising the steps of:
 a) providing a moulding form for injection moulding;
 b) injecting silicone into the form;
 c) curing the silicone;
 d) releasing the product from the moulding form; and
 e) rolling the urisheath to include the strips. During this operation the on side of the legs of the strips are twisted down on the surface of the sheaths to secure a rolling without wrinkles on the strip.

In the preparation of the rolled tubular section, the strips will typically be applied in the un-rolled condition. Thereafter, the tubular section is rolled, so that the strips are placed in between the inside and outside of the tube. Hereby, each of the strips forms a path along the tubular section.

In one embodiment, each of those paths is parallel to the longitudinal axis of the unrolled tubular section—hereby securing an even draw.

However, when placing the strips parallel to the longitudinal axis of the unrolled section, the rolled tubular section will have an un-even outer rim, thicker where the strips are, thinner at places along the rim, where the strips are absent. In order to obtain a smoother surface of the rolled tubular section, at least one path of the strip is a spiral shape.

The present invention also relates to a rolled urisheath comprising a body portion and a strip portion wherein the strip portion is attached to the body portion in an attachment zone.

The unrolling strip is considered to be a major benefit on the product, because that the application of the urisheath on the penis can be done by people with reduced hand function or by nurses wearing gloves. This unrolling strip also secures a smooth an easy unrolling of the product, giving improved security of leakage when wearing the product.

It is preferred that the thickness of the strip is about 0.06 mm. To secure flow of material through such thin product, the injection moulding form can be provided with more than one inlet ports.

Varying the thickness and the width can also vary the elastic feeling along the length of the strip. It is preferred to have rather large thickness of the handle part (e.g. 0.20 to 2.0 mm) and low thickness on the part alongside the shaft part (0.05 to 0.20 mm). This is in order to have a good rolling of the sheath.

Throughout the present specification, reference has been made to urisheath. However, the same technology can be used to injection mould a condom. Consequently, the present invention also relates to an injection moulding form for a condom and a condom semi-manufacture product.

EXAMPLES

Example 1

Double strip moulded almost separately from the urisheath only moulded together with the distant end of the urisheath.

This example requires large tooling and still leaves the strip not fully attached to the product.

Example 2

Strip moulded along sheath part of and attached by a thinner part that will be torn as the urisheath is unrolled. There can also be a perforation combined or instead of the thin part.

This example makes it easy to handle the urisheaths in the subsequent steps of the production. The difficult part here is to mould the combined handle function for the 2 legs of strip. The handle shall preferentially be of a length so that it ends before the end of the tip.

This can be done in several ways:
either the tooling is made with more than 3 movable parts;
the tooling is made with 3 movable parts, but the strip (or strip handle) is attached to the tip of the urisheath, and shall be cut off in a following step;
the strip is made with 2 legs and the combined handle part is obtained by attaching these 2 legs to each other in a following step. They can be attached by mechanical or chemical means;

The combined handle part is made on top of the tip. However, this alternative gives an unrolling strip, which is longer than usually needed.

Example 3

To manufacture a urisheath we take a C6-540 (shore 40 A hardness) silicone from Dow Corning and injection into a mould, such that the thickness of the sheath portion is 0.20 mm and the strip portion is 0.10 mm in the lower part of the urisheath, and thickness of the sheath portion is 0.40 mm and the strip portion is 0.15 mm at the upper part of the urisheath close to the bellow part. The width of the strip is 8 mm along the length of the sheath part. The varying thickness of the strip provides for giving a not too elastic feeling when the user starts the unrolling with the strip. The thinner strip at the bottom secures that the strip is not giving a too high unevenness of the sheath portion in its rolled position, which possibly could give uneven unrolling and wrinkles of the sheath when unrolled by the user. The handle part of the strip is made in a thickness of e.g. 0.6 mm and shall secure a god grip also for people with reduced hand function.

Example 4

In another example the urisheath and the strip is made in two different silicones by two-component injection moulding. The sheath part is moulded as in example 1 in C6-540 silicone from Dow Corning. The strip part is made in C6-570 silicone from Dow Corning. This is a silicone of higher hardness (shore 70 A hardness). The strip part shall be made in a thickness of 0.06 mm at the lower part and a thickness of 0.10 mm at the upper part close to the bellow part. The width of the strip is still 8 mm along the length of the sheath part. The thinner strip reduces the possibility for uneven unrolling and wrinkles further compared to example 1, but is off cause also more complicated and costly to produce. The handle part of the strip is made in a thickness of e.g. 0.4 mm and shall secure a good grip also for people with reduced hand function.

FIGURES

Further advantages of the present invention will be understood in the following detailed description wherein the invention will be described with reference to the enclosed figures. The figures and detailed description serves as examples only and should not be understood as limiting the scope of the invention.

Figure 1:
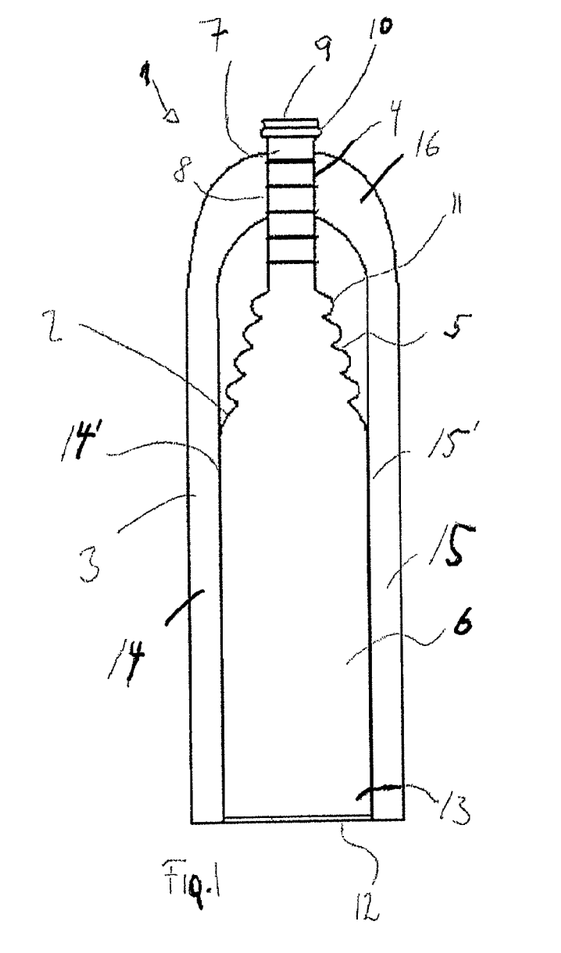
FIGS. 1 and 2 illustrate a first embodiment of the invention seen from the side in two different angles.

FIGS. 1 and 2 shows one embodiment of an injection moulded semi-manufactured urisheath assembly 1 according to the invention.

An urisheath 2 and a strip portion 3 form the urisheath assembly 1.

The urisheath consist of a tip part 4, a shoulder part 5 and a body part 6.

The tip part 4 extends in distance A from the shoulder part 5 towards an outlet end 9 and is adapted to be connected to a discharge tube (not shown). A drainage tube 7 whereon five round going friction ribs 8 are formed makes up the tip part. The ribs provide frictional means so that a user, e.g. the patient or nurse, can control the drainage tube without loosing the grip. At the outlet end 9 of the drainage tube there is provided a protruding connection rib 10. This connection rib protrudes further outwards in a radial distance from the drainage tube than the round going friction ribs 8. The connection rib function provides frictional engagement when the drainage tube and the discharge tube are connected.

The shoulder part 5 connects the body part to the tip part. In the present embodiment the shoulder part is formed with four round going bulbous rings 11.

The body part 6 is formed as a tubular section extending from the shoulder part to a mounting opening 12. The body part is divided into a root portion 13, which extends in a distance B from the mounting opening 12 towards the outlet end 9 and a centred part 14 extending in a distance C from the root portion 13 towards the outlet end 9.

The strip portion 3 is formed as two parallel strips 14, 15 extending from the mounting opening 12 towards the outlet end 9, terminating approximately at the beginning of the tip part. A handle 16 in the shape of an arc formed bridge strip connects the ends of the two strips closest to the outlet end. The strip portion 3 is releasable attached to the urisheath via the respective sides, facing toward the urisheath, of the two parallel strips which extends along the body part by longitudinal attachment zones 14', 15'.

The attachment zones are typically formed as weakened zones, i.e. having lower tear strength than the strip portion 3 and the urisheath 2 respectively. During injection moulding these attachment zones may be provided in a number of different ways. For example it may be provided as a decrease in the thickness of the material compared to the thickness of the parallel strips and/or the thickness of the wall of the body part. Alternatively they may be provided as two lines of perforations extending along the body part or as a few, for example one or two, connection points between the parallel strips and the urisheath.

Thus when the urisheath is held in a fixed position and the strip portion is pulled the urisheath assembly will be separated along the attachment zones.

Furthermore, as can be seen in FIG. 2 the strip portion is formed with a bend 17. This allows the strip portion to have length with is shorter than the extent of the urisheath, while at the same time connecting the two parallel strips 14 and 15 with a continuous handle 16 as the handle is guided around the tip part 4.

Figure 3:
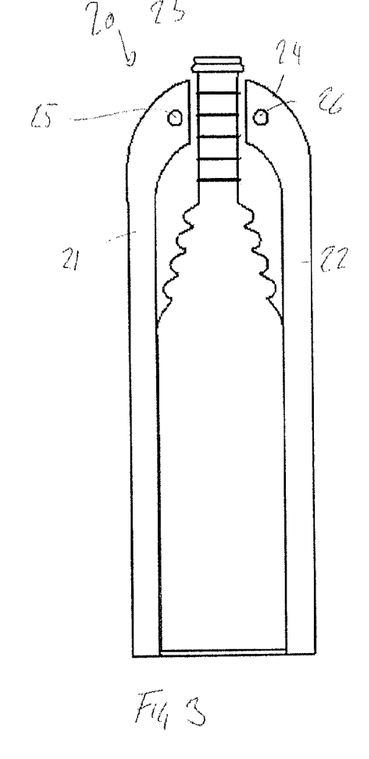
FIGS. 3, 4 and 5 illustrates a second embodiment of the invention seen from the side in two different angles and in perspective from above.
Figures 4, 5:
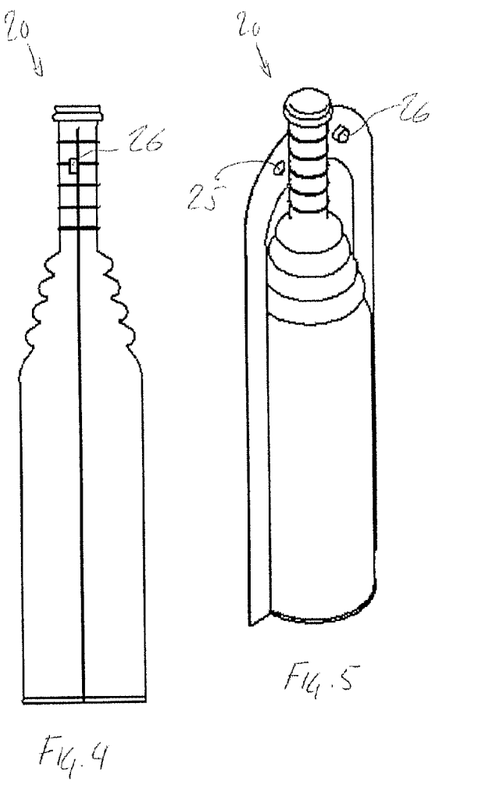

FIGS. 3, 4 and 5 show an alternative embodiment injection moulded semi-manufactured urisheath assembly 20 according to the invention.

In this embodiment the urisheath is the same as in FIGS. 1 and 2, however, the strip portion is formed as two individual strips 21 and 22. The two individual strips are connectable via connection ends 23 and 24 which are formed with locking means in form of a through going hole 25 provided in the first connection end and a tab 26 on the second connection end 24. When used the tab is pushed into the through going hole locking the two connection ends together thereby forming a handle (the handle not shown assembled).

During injection moulding the strip portion is attached to the urisheath in a similar way as described with respect to FIGS. 1 and 2.

Figure 6:
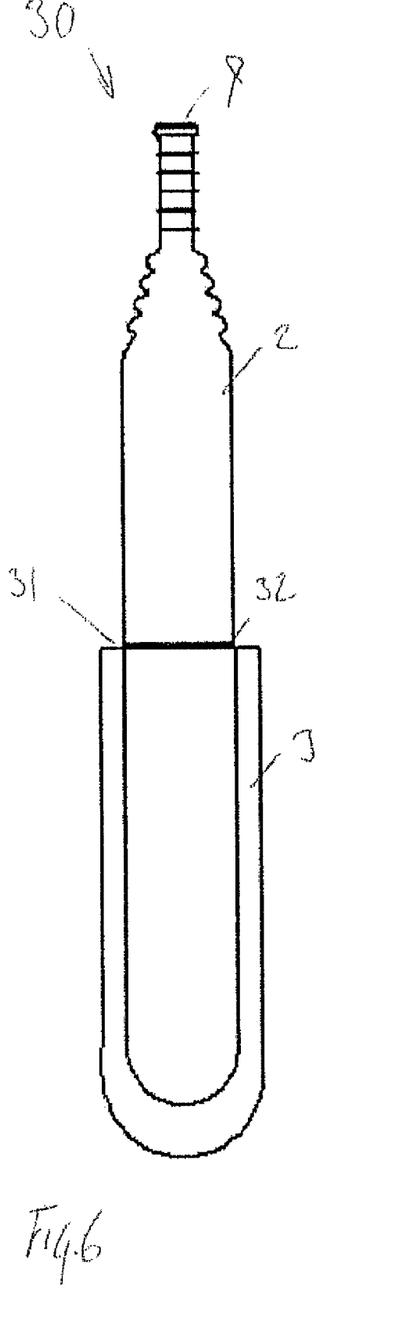
FIGS. 6 and 7 illustrates a third embodiment of the invention seen from the side in two different angles.
Figure 7:
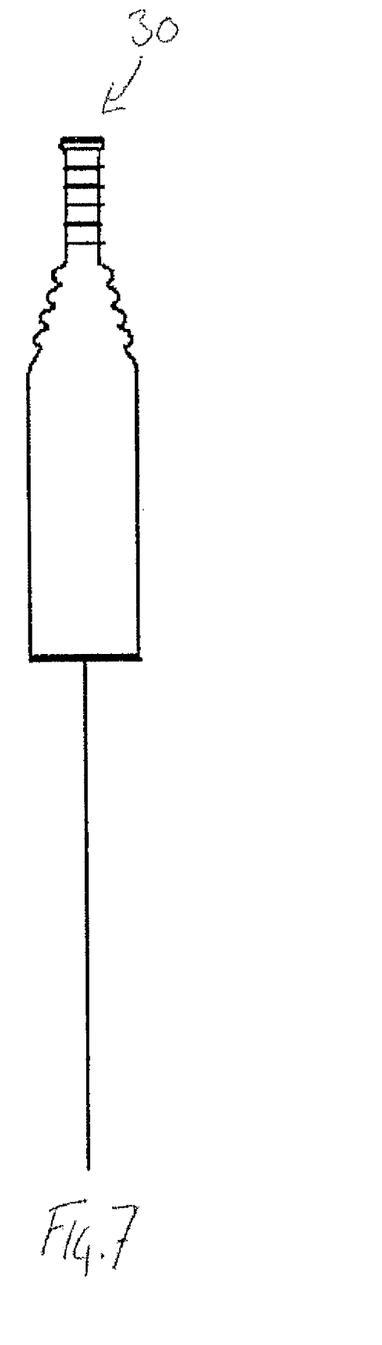

FIGS. 6 and 7 shows yet another embodiment injection moulded semi-manufactured urisheath assembly 30 according to the invention.

The strip portion 3 and the urisheath 2 correspond to the part as described in FIGS. 1 and 2, however, during injection moulding they have been assembled differently.

The strip portion 3 is attached to the urisheath 2 at attachment points 31 and 32 at the root portion of the urisheath and extends in a direction from the root portion and away from the outlet end 9 of the urisheath.

Figure 8:
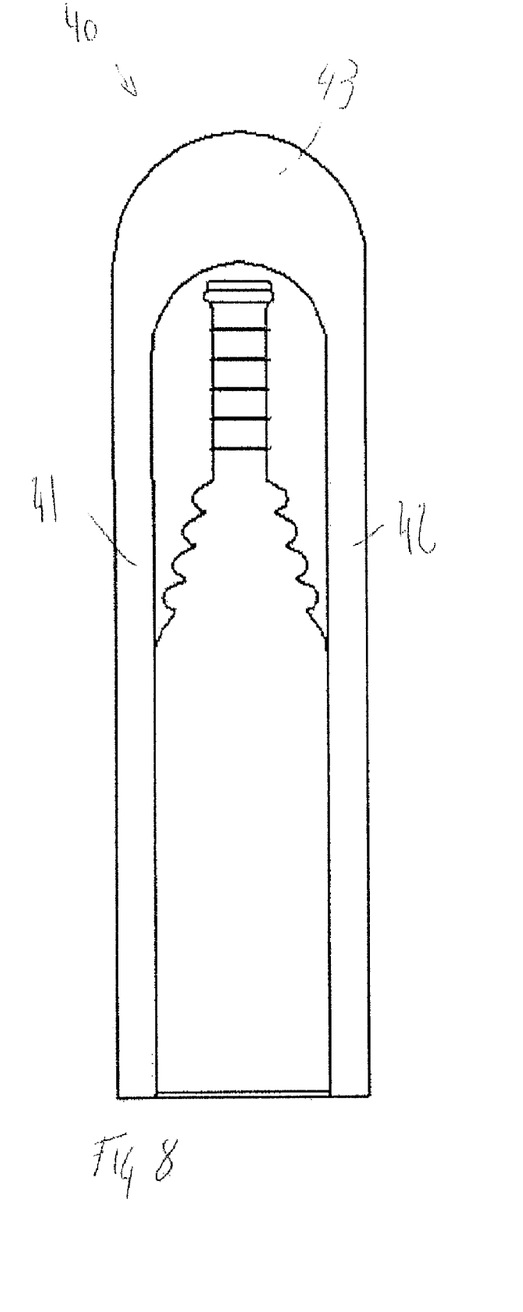
FIGS. 8 and 9 illustrates a fourth embodiment of the invention seen from the side in two different angles.
Figure 9:
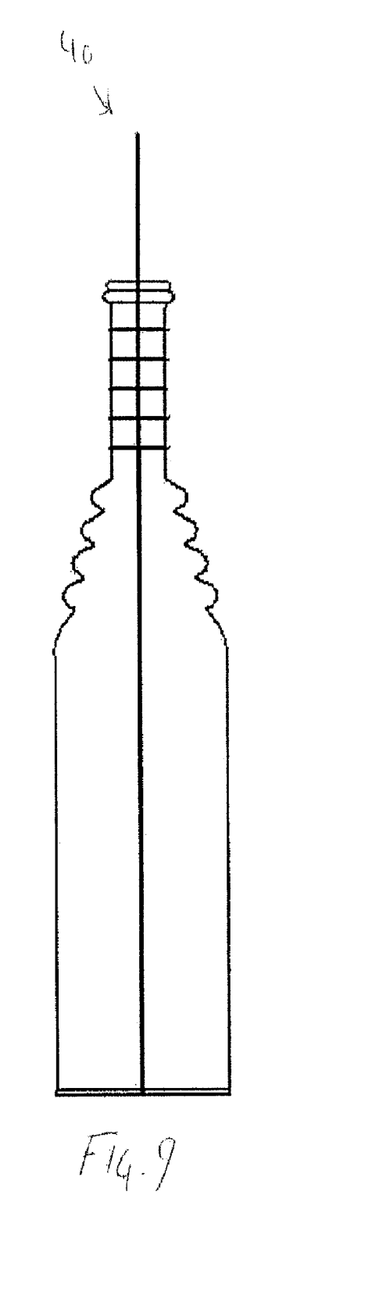

Yet another embodiment of an injection moulded semi-manufactured urisheath assembly 40 according to the invention is shown in FIGS. 8 and 9. In this embodiment the parallel strips 41 and 42 extends from the root portion of the urisheath almost to the outlet end of the tip part. Thus it is not necessary to provide the parallel strip with a bend, such as described in FIGS. 1 and 2, as the handle 43 connecting the two parallel strips is arranged past the tip part.

Figure 10:
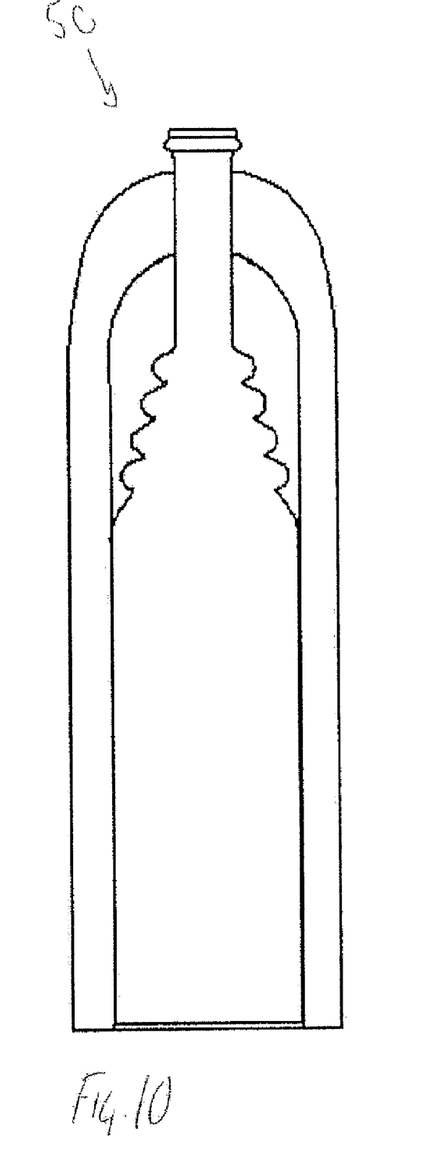
FIGS. 10 and 11 illustrate a third embodiment of the invention seen from the side in two different angles.
Figure 11:
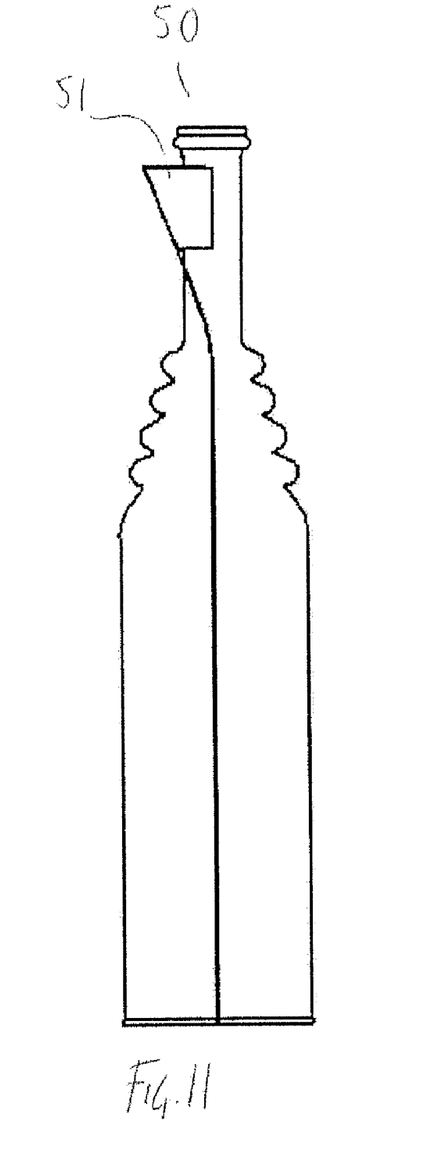

In a further embodiment of an injection moulded semi-manufactured urisheath assembly 50 according to the invention is shown in FIGS. 10 and 11. This embodiment is almost identical to the one shown in FIGS. 1 and 2 except that tabs 51 and 52 (tab 52 is not seen in the drawing as the tab 51 covers it) connects the handle 16 and the tip part 4. These tabs results of the injection moulding process as they are created in order to provided and even distribution and even flow and curing of the urisheath assembly material during production. Tabs 51 and 52 will often be cut away before selling the product.

The invention claimed is:

1. A method for producing a urisheath comprising:
   providing a moulding form adapted for injection moulding;
   injecting silicone into the form;
   curing the silicone, thereby defining the urisheath, the urisheath comprising a body portion, the body portion comprising:
   a root part, a centered part, and a tip part; and
   a strip portion attached to the body portion in an attachment zone, the attachment zone comprising a weakened zone;
   releasing the product from the moulding form; and
   rolling the urisheath to include the strip portion.

2. An injection moulding form for a urisheath comprising: a cavity for a body portion, the body portion comprising a root part, a centered part, and a tip part;
   a cavity for a strip portion; and
   a cavity for an attachment zone connecting the strip portion to the body portion, adapted such that the attachment zone comprises a weakened zone.

3. The injection moulding form according to claim 2, wherein the cavity for the strip portion comprises a cavity defining one strip.

4. The injection moulding form according to claim 3, wherein the connection between the cavity for the strip portion and the cavity for the body portion is at the root part.

5. The injection moulding form according to claim 4, wherein the form comprises three solid parts: a core part, an upper shield part and a lower shield part.

6. The injection moulding form according to claim 5, further comprising a cavity for a handle.

7. The injection moulding form according to claim 6, wherein the handle cavity is formed between the upper shield part and the lower shield part.

8. The injection moulding form according to claim 6, wherein the handle cavity is formed within one of the upper shield part and the lower shield part.

9. The injection moulding form according to claim 6, wherein the handle cavity is formed between one of the upper shield part, the lower shield and a $4^{th}$ form element.

10. The injection moulding form according to claim 2, wherein the cavity for the strip portion comprises two strips.

11. The injection moulding form according to claim 10, further comprising a cavity for a handle connecting two strips.

12. The injection moulding form according to claim 11, wherein the handle cavity is formed between the upper shield part and the lower shield part.

13. The injection moulding form according to claim 11, wherein the handle cavity is formed within one of the upper shield part and the lower shield part.

14. The injection moulding form according to claim 11, wherein the handle cavity is formed between one of the upper shield part, the lower shield and a $4^{th}$ form element.

* * * * *

UNITED STATES PATENT AND TRADEMARK OFFICE
CERTIFICATE OF CORRECTION

| | |
|---|---|
| PATENT NO. | : 8,961,854 B2 |
| APPLICATION NO. | : 13/160090 |
| DATED | : February 24, 2015 |
| INVENTOR(S) | : Henrik Lindenskov Nielsen et al. |

It is certified that error appears in the above-identified patent and that said Letters Patent is hereby corrected as shown below:

Title Page 1, Item (73) Assignee:
Change "Nolato Meditech AG" to -- NOLATO MEDITECH AB --.

Title Page 1, Item (57) Abstract:
Line 4, change "molding" to -- moulding --;
Line 5, change "molding" to -- moulding --;
Line 6, change "molding" to -- moulding --; and
Line 7, change "molding" (both occurrences) to -- moulding --.

Signed and Sealed this
Second Day of June, 2015

Michelle K. Lee
*Director of the United States Patent and Trademark Office*